(12) United States Patent
Krause

(10) Patent No.: US 9,689,851 B2
(45) Date of Patent: Jun. 27, 2017

(54) HEATABLE GAS ANALYSIS DEVICE

(71) Applicant: Siemens Aktiengesellschaft, Munich (DE)

(72) Inventor: Peter Krause, Karlsruhe (DE)

(73) Assignee: Siemens Aktiengesellschaft, Munich (DE)

(*) Notice: Subject to any disclaimer, the term of this patent is extended or adjusted under 35 U.S.C. 154(b) by 388 days.

(21) Appl. No.: 14/391,043

(22) PCT Filed: Mar. 26, 2013

(86) PCT No.: PCT/EP2013/056359
§ 371 (c)(1),
(2) Date: Oct. 7, 2014

(87) PCT Pub. No.: WO2013/156277
PCT Pub. Date: Oct. 24, 2013

(65) Prior Publication Data
US 2015/0139274 A1    May 21, 2015

(30) Foreign Application Priority Data

Apr. 20, 2012 (DE) .................. 10 2012 206 512

(51) Int. Cl.
*G01K 3/00* (2006.01)
*G01N 33/00* (2006.01)
(Continued)

(52) U.S. Cl.
CPC ........... *G01N 33/0016* (2013.01); *G01K 3/10* (2013.01); *G01N 30/30* (2013.01); *G01N 30/54* (2013.01);
(Continued)

(58) Field of Classification Search
USPC ...................... 374/137, 1, 110, 166
See application file for complete search history.

(56) References Cited

U.S. PATENT DOCUMENTS

| 5,028,243 A | 7/1991 | Rubey |
| 5,665,314 A | 9/1997 | Berger et al. |

(Continued)

FOREIGN PATENT DOCUMENTS

| DE | 4308936 A1 | 9/1994 |
| DE | 19601571 A1 | 7/1997 |
| DE | 69533019 T2 | 4/2005 |

OTHER PUBLICATIONS

Gritti et al; "Complete Temperature Profiles in Ultra-High-Pressure Liquid Chromatography Columns"; American Chemical Society; Analytical Chemistry, vol. 80; No. 13; pp. pp 5009-5020; XP002698381; 2008; US; May 6, 2008.

*Primary Examiner* — Mirellys Jagan
(74) *Attorney, Agent, or Firm* — Cozen O'Connor

(57) ABSTRACT

A heatable gas analysis device which is monitored in a simply way, wherein a gas analysis device contains a monitoring unit which, after the device is switched on and until a predefined operating temperature is reached, generates a two-dimensional temperature profile from temperature progressions measured at different measuring points within the device, in which temperature profile one dimension indicates time and another dimension indicates the different measuring points, where the monitoring unit compares the temperature profile to a reference temperature profile generated and stored under reference conditions and, in the event of any deviation exceeding a predefined amount, generates an error message.

5 Claims, 1 Drawing Sheet

(51) Int. Cl.
  *G01N 30/30*  (2006.01)
  *G01N 30/54*  (2006.01)
  *G01K 3/10*  (2006.01)

(52) U.S. Cl.
  CPC ............... *G01N 2030/3076* (2013.01); *G01N 2201/0612* (2013.01)

(56) References Cited

U.S. PATENT DOCUMENTS

| | | | |
|---|---|---|---|
| 2004/0052293 A1* | 3/2004 | Sutherland | G01N 25/4846 374/100 |
| 2005/0143897 A1* | 6/2005 | Ripper | F01N 11/002 701/101 |
| 2014/0230519 A1* | 8/2014 | Kleiner | G01F 25/0053 73/1.16 |
| 2015/0233771 A1* | 8/2015 | Uno | G01K 11/3206 374/4 |

* cited by examiner

HEATABLE GAS ANALYSIS DEVICE

REFERENCE TO RELATED APPLICATIONS

This is a U.S. national stage of application No. PCT/EP2013/056359 filed 26 Mar. 2013. Priority is claimed on German Application No. 102012206512.1 filed 20 Apr. 2012, the content of which is incorporated herein by reference in its entirety.

BACKGROUND OF THE INVENTION

1. Field of the Invention

The invention relates to a heatable gas analysis device.

2. Description of the Related Art

In gas analysis, heatable analysis devices are used when the gas to be analyzed (i.e., the measurement gas) contains moisture, and when condensation in the device is meant to be prevented. To this end, for example, the entire device may be heated by circulated-air, so that the gas paths in the device are brought to a predetermined uniform operating temperature. In this case, at the interfaces with the environment of the device, i.e., in the regions of the measurement gas input and output, additional heaters may be provided for the gas paths. There are also gas analyzers comprising gas sensors, in particular based on semiconductor metal oxides, which need to be heated in order to be able to perform meaningful measurements. In gas chromatographs, heating of the separating column is often necessary to achieve the desired separation properties, or the sample to be analyzed is a liquid that needs to be evaporated before it enters the separating column. Since conventional gas analysis methods are generally temperature-sensitive, not least the influence of external temperature can be reduced by heating the analysis device, and the measurement result can thereby be stabilized.

DE 196 01 571 A1 discloses a gas chromatograph comprising two separately thermally regulatable separating columns, of which one separating column is arranged in an oven and the other separating column is coiled outside the oven on an electrically heatable heating body.

In a method known from DE 43 08 936 A1, in order to calibrate a measurement device, such as a gas analysis device, in which the sensitivity and zero point can vary during operation because of heating of the physical part after switching on and because of temperature gradients, a plurality of calibration values are measured at time intervals. With a predetermined number of most recently measured calibration values, via a nonlinear function, future calibration values, with which the measurement values are corrected, are calculated.

From DE 695 33 019 T2, it is known to control the temperature in a predetermined zone of an analytical instrument by subjecting a heating fluid to an exothermic chemical reaction in a convertor and delivering the heat generated thereby into the zone. The flow of heating fluid into the convertor is regulated as a function of the temperature measured in the zone. It is additionally possible to use a cooling fluid for cooling, which is subjected to an endothermic chemical reaction.

Here and in what follows, heating of the gas analysis device is not necessarily intended to mean heating of the entire device. In most cases, the heating is restricted to the analysis part or module, with the measurement components contained therein directly recording the measurement gas, through which the measurement gas flows. In the case of a non-dispersive infrared (NDIR) gas analyzer, these are for example an infrared radiator, a measurement-gas cell and optionally reference-gas cell, and an opto-pneumatic detector arrangement.

After the analysis device is switched on, it is a general practice to wait until the device, or the analysis part, has reached operating temperature, the temperature having to lie within a specified tolerance so that the analysis part is capable of measurement.

Correct construction and the stability of the mechanical components of the analysis part are indispensable for correct measurement value acquisition. If, during manufacture of the device, the construction does not correspond to the specification, or the mechanical stability weakens during subsequent operation, this can have a serious effect on the measurement value acquisition. Testing is therefore generally performed by visual inspection with the device open. Unacceptable deviations can be identified by calibration with a test gas, and leaks can be identified by a pressure test.

SUMMARY OF THE INVENTION

It is therefore an object of the invention to improve the testing of a gas analysis device with respect to its intended operating state in a simple manner.

This and other objects and advantages are achieved in accordance with the invention by a heatable gas analysis device that comprises a testing unit, which is configured to produce, from temperature variations measured at various measurement points inside the device after the device is switched on and until a predetermined operating temperature is reached, a two-dimensional temperature profile in which one dimension denotes the time and another dimension denotes the various measurement points, and which is furthermore configured to compare the temperature profile with a reference temperature profile produced under reference conditions and stored, and to generate an error message in the event of a difference exceeding a predetermined amount.

In order to be able to regulate the electrical heating of the gas analysis device, temperature sensors need to be provided. Certain components of the device, such as an infrared radiator, laser diodes, detector arrangements, or electrical components and circuits, may comprise their own temperature sensors for regulation and/or monitoring. In order to measure the temperature variations in the device, after it has been switched on, it is possible to use these temperature sensors that are provided anyway, or optionally further temperature sensors provided for this purpose.

At the time of switching on, the temperatures are generally the same at all points of the device. This also applies in most cases when the device, or the heated device part, is heated to operating temperature, because even in the event of a fault in the device a temperature equilibrium will be established sooner or later. Thus, if the device has reached operating temperature, device faults can be identified with the aid of the measured temperatures only in particular individual cases. Such individual cases are, for example, defectively functioning heaters or electrical components with their own temperature sensors. Defective screwing of mechanical holders, on the other hand, will not be identifiable based on the temperature reached.

In contrast thereto, however, after the device is switched on and until the operating temperature is reached, different temperature variations occur at different points within the device, this depending on the mechanical construction and state of the device per se and in the vicinity of these points. For example, because of the increased thermal resistance between the holders, the aforementioned defective screwing will lead to a delay in the temperature rise of structural parts lying behind this point in the direction of the heat flow. The heat propagates differently until a temperature equilibrium is reached inside the device, and the temperature is measured only at a limited number of measurement points. As a result, the measured temperature variations on their own do not provide information about the state of the device. In their totality as a two-dimensional temperature profile, however, they give an image, or a corresponding fingerprint, dependent on the state of the device. In accordance with the invention, such a thermodynamic fingerprint is therefore obtained after the device is switched on, and is compared with a reference fingerprint produced under reference conditions. This reference fingerprint may be taken from the device itself, such as immediately after its production or after a revision, or it may come from a reference device of the same design. If the difference between the recorded fingerprint and the reference fingerprint exceeds a predetermined amount, an error message is generated.

Preferably, in the two-dimensional temperature profile with time as one dimension and the various measurement points as the other dimension, the time is subdivided into discrete time intervals, the temperature profile containing a temperature value for each time interval and each measurement point, and thus forming a pattern consisting of the temperature values. The comparison between the respectively currently recorded temperature profile (i.e., a fingerprint) and the reference temperature profile (i.e., a reference fingerprint) may then be performed by using pattern recognition methods. For certain identified device faults, the pattern obtained, or the difference pattern of the temperature profile and the reference temperature profile, may be stored and used for the identification of future faults.

Preferably, the device in accordance with the invention comprises a display for visualization and/or a communication interface for transmitting the pattern and/or the difference between the patterns of the temperature profile and of the reference temperature profile.

The testing of the analysis device is performed automatically. The device does not need to be opened for this purpose, and the analysis module does not need to be removed. The heated device in any case contains a more or less large number of temperature sensors. As a result, the additional device outlay for testing the device with the aid of the temperature profile is minimal.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention will be explained below with reference to the figures of the drawing with the aid of exemplary embodiments; in which.

DETAILED DESCRIPTION OF THE PREFERRED EMBODIMENTS

Figure 1:
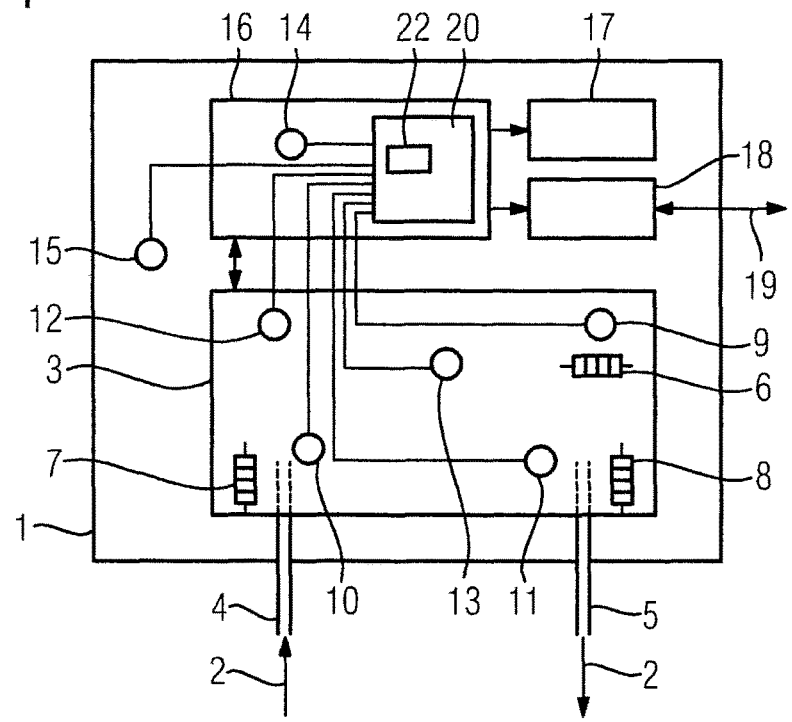
FIG. 1 shows an outline block diagram of the device in accordance with the invention.

FIG. 1 shows a heatable gas analysis device 1 comprising an analysis part 3, through which a measurement gas 2 flows and which in this case has measurement components (not shown) for direct measurement gas recording. The measurement gas 2 enters the analysis part 3 from the outside through a measurement gas input 4, and exits through a measurement gas output 5. Here, the heating of the device 1 is restricted to the analysis part 3, and comprises an electrical heating device 6 inside the analysis part 3 as well as two further heating devices 7 and 8 for heating the measurement gas input 4 and the measurement gas output 5. Depending on the measurement principle, some of the measurement components in the analysis part 3 may have their own heating devices. In order to regulate the heating devices 6, 7, 8, temperature sensors 9, 10, 11 are arranged at or in the vicinity thereof. Furthermore, further temperature sensors 12, 13, 14, 15 may be provided at different measurement points, both in the analysis part 3 and outside the latter in the device 1. All or some of these temperature sensors 12 to 15 may be used for temperature monitoring or as a part of temperature regulation of device components, such as for regulating the radiation power of an infrared radiator in the analysis part or for monitoring a temperature-sensitive electrical control and evaluation unit 16. The control and evaluation unit 16 controls the analysis part 3, processes the measurement values of the measurement gas analysis delivered by the analysis part 3, and outputs the processed measurement values via a display 17 and/or a communication interface 18, such as onto a field bus 19.

The control and evaluation unit 16 contains a testing unit 20, which evaluates the temperature measurement values delivered by the temperature sensors 9 to 15 and produces a two-dimensional temperature profile from the temperature variations measured at the various measurement points of the temperature sensors 9 to 15, after the device is switched on and until a predetermined operating temperature is reached. The predetermined operating temperature may, for example, be regarded as having been reached when temperatures measured by one, preferably a plurality, or all of the temperature sensors 9 to 15 in the analysis part 3 lie within a specified tolerance range around the setpoint value of the operating temperature. If the operating temperature is not reached within a predetermined time, an error message may be output.

Figure 2:
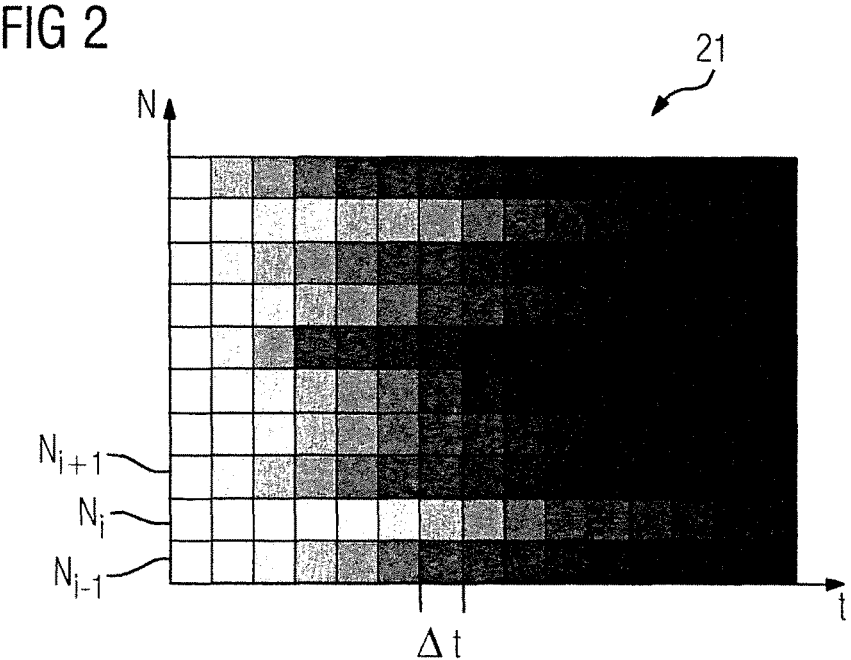
FIG. 2 shows a simplified graphical plot of an exemplary temperature profile that is produced.

FIG. 2 shows a simplified graphical plot of an exemplary temperature profile 21 produced, in which one dimension t denotes the time and the other dimension N denotes the various temperature measurement points $N_i$, or the temperature sensors located there. The example shown in FIG. 2 is based on a larger number of temperature measurement points than the number of temperature sensors 9 to 15 shown in FIG. 1.

For the temperature profile 21, the temperature variations are stored with discrete times, by subdividing the time t into discrete time intervals $\Delta t$ and the temperature profile 21 containing, for each time interval $\Delta t$ and each measurement point $N_i$, a temperature value that is represented here by an individual gray value. The temperature profile 21 therefore forms a pattern consisting of the temperature values.

After production and successful testing of the device 1, a reference temperature profile is produced and is stored in a memory 22 of the device 1. Such a reference temperature profile may also be produced from a reference device of the same design, and for example transmitted by the communication interface 18 to the memory 22 of other devices 1 of the same device series.

The testing unit 20 compares the temperature profile 21 newly produced after each time that the device 1 is switched on with the reference temperature profile produced under reference conditions and stored, and in the event of a difference exceeding a predetermined amount generates an error message, which is output via the display 17 and/or the communication interface 18. Pattern recognition methods known per se may be used for the comparison.

Thus, while there have been shown, described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A heatable gas analysis device comprising:
a testing unit configured to produce, from temperature variations measured at various measurement points inside the device after the device is switched on and until a predetermined operating temperature is reached, a two-dimensional temperature profile in which one dimension denotes time and another dimension denotes a plurality of the various measurement points, and further configured to compare the two-dimensional temperature profile with a reference temperature profile produced under reference conditions and stored, and to generate an error message in an event of a difference between the two-dimensional temperature profile and the reference temperature profile exceeding a predetermined amount.

2. The gas analysis device as claimed in claim 1, wherein the time is subdivided into discrete time intervals and the two-dimensional temperature profile contains a temperature value for each time interval of the discrete time intervals and each measurement point of the plurality of the various measurement points, so that the two-dimensional temperature profile forms a pattern consisting of temperature values, and wherein the testing unit performs comparisons based on pattern recognition.

3. The gas analysis device as claimed in claim 2, further comprising:
a communication interface for transmitting at least one of
(i) the pattern consisting of the temperature values and
(ii) a difference between patterns of the two-dimensional temperature profile and a pattern of the reference temperature profile.

4. The gas analysis device as claimed in claim 2, further comprising:
a display for visualizing at least one of (i) the pattern consisting of the temperature values and (ii) a difference between patterns of the two-dimensional temperature profile and a pattern of the reference temperature profile.

5. The gas analysis device as claimed in claim 4, further comprising:
a communication interface for transmitting at least one of
(i) the pattern consisting of the temperature values and
(ii) the difference between the patterns of the two-dimensional temperature profile and the pattern of the reference temperature profile.

\* \* \* \* \*